US006787179B2

(12) United States Patent
Timm et al.

(10) Patent No.: US 6,787,179 B2
(45) Date of Patent: Sep. 7, 2004

(54) STERILIZATION OF BIOACTIVE COATINGS

(75) Inventors: Debra A. Timm, Foothill Ranch, CA (US); Henry K. Hui, Laguna Niguel, CA (US); Mark B. Roller, North Brunswick, NJ (US); Mora C. Melican, Bridgewater, NJ (US); Syed Hossainy, Fremont, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/897,657

(22) Filed: Jun. 29, 2001

(65) Prior Publication Data

US 2003/0175408 A1 Sep. 18, 2003

(51) Int. Cl.[7] .......................... A61L 27/00; A61L 27/28; A61L 27/54; A61L 2/00; B05D 3/04
(52) U.S. Cl. .................... 427/2.24; 427/2.25; 427/2.26; 427/2.27; 427/2.28; 427/2.29; 427/2.3; 427/487; 427/488; 427/489; 427/490; 427/491; 427/533; 427/534; 427/535; 427/536; 427/372.2
(58) Field of Search ................................. 427/2.1, 2.24, 427/2.25, 2.26, 2.27, 2.28, 2.29, 2.3, 487, 488, 489, 490, 491, 533, 536, 372.2

(56) References Cited

U.S. PATENT DOCUMENTS

| | | | |
|---|---|---|---|
| 4,656,083 A | | 4/1987 | Hoffman et al. |
| 4,728,564 A | * | 3/1988 | Akagi et al. ................ 428/336 |
| 4,743,258 A | * | 5/1988 | Ikada et al. ................. 427/2.25 |
| 5,034,265 A | | 7/1991 | Hoffman et al. |
| 5,108,776 A | * | 4/1992 | Goldberg et al. .......... 427/2.24 |
| 5,132,108 A | | 7/1992 | Narayanan et al. |
| 5,244,654 A | | 9/1993 | Narayanan |
| 5,409,696 A | | 4/1995 | Narayanan et al. |
| 5,643,464 A | | 7/1997 | Rhee et al. |
| 5,656,238 A | * | 8/1997 | Spencer et al. ........ 422/186.05 |
| 5,866,113 A | * | 2/1999 | Hendriks et al. ........... 424/486 |
| 6,149,878 A | * | 11/2000 | Jacob et al. ................ 204/164 |
| 6,245,537 B1 | * | 6/2001 | Williams et al. ............ 424/422 |

FOREIGN PATENT DOCUMENTS

| | | |
|---|---|---|
| DE | 199 44 631 | 3/2001 |
| EP | 0 233 708 | 8/1987 |
| WO | WO 95/04609 | 2/1995 |

OTHER PUBLICATIONS

J. Palmaz, et al. "Intravascular Stents," Advances in Vascular Surgery, vol. 1, pp. 107–135, 1993.
J. Palmaz, "Intravascular Stents: Tissue–Stent Interactions and Design Considerations," American Journal of Radiology, 160:613–618, 1993.
V. DePalma, et al., "Investigation of Three–surface Properties of Several Metals and Their Relations to Blood Compatibility," J. Biomed. Mater. Res. Symposium, No. 3, pp. 37–75, 1972.
J. Kocsis, et al., "Heparin–Coated Stents," Journal of Long–Term Effects of Medical Implants, 10(1&2):19–45, 2000.
European Search Report related to application EP 02 25 4563, completed on Sep. 30, 2002, Germany office.

* cited by examiner

Primary Examiner—Shrive P. Beck
Assistant Examiner—Jennifer Kolb Michener

(57) ABSTRACT

The invention provides a method for single-step surface modification, grafting and sterilization for bio-active coating on materials and biomaterials used in medical devices, such as catheters, tissue engineering scaffolds, or drug delivery carrier materials. This may include any medical device or implantable that could benefit from improved antithrombogenic and biocompatible surfaces. Other relevant device examples may include heparin or urokinase coated stents to reduce clotting and restenosis, dental or ophthamological implants. These materials may be comprised of a variety of polymeric compositions such as, polyurethane, polyester, polytetrafluoroethylene, polyethylene, polymethylmethacrylate, polyHEMA, polyvinyl alcohol, polysiloxanes, polylactic or glycolic acids, polycaprolactone, etc. The substrates can also be metal, ceramics or biologically derived materials.

23 Claims, 1 Drawing Sheet

STERILIZATION OF BIOACTIVE COATINGS

BACKGROUND OF THE INVENTION

1. Field of the Invention

The invention relates to coatings and sterilization of coatings for devices with a medical use.

2. Description of the Related Art

Many polymeric materials can be used as medical device and implant fabrication materials. To improve the biocompatibility of these materials, surface modifications and coatings are used to reduce thrombosis or rejection. The modification or coating of these materials require several processing steps to accomplish the material coating. Substrates modified by each of these methods also require a sterilization method to finalize the product for use by the manufacturer. This introduces the issue of stability of the modified surface under the sterilization process, as the coating materials may not be compatible with traditional sterilization methods.

Different methods of surface modification have been documented in the literature for the purpose of favorable host-material response. Several U.S. patent documents provide means to coat biomedical devices, particularly those in contact with blood such as stents, but do not address the problem of subsequent sterilization (U.S. Pat. Nos. 4,656,083; 5,034,265; 5,132,108; 5,244,654; and 5,409,696) Palmaz et al, in a review of intravascular stents, is skeptical of the use of stent coatings (Palmaz, J., F. Rivera and C. Encamacion. Intravascular Stents, *Adv. Vasc. Surg.*, 1993, 1:107–135). However, Kocsis et al. report that the use of heparin-coated stents was effective to reduce thrombogenicity of the stent surface (Kocsis, J., G. Llanos and E. Holmer. Heparin-Coated Stents, *J. of Long-Term Effects of Medical Implants*, 2000, 10 19–45)

Typical modifications include hydrophilic and/or hydrogel coatings such as polyvinyl pyrrolidone (PVP), polyethylene glycol (PEG), or Hyaluronic acid (HA), on the surface of cardiovascular implants (stents and pacemakers) or indwelling medical devices, topical wound healing applications, contact lenses, intraocular lenses, etc. Hydrophobic or lubricious coatings are used for medical devices such as coronary or neurovascular guidewires, sutures, needles, catheters and trocars. Bio-active coatings are used for directed cell response such as cell adhesion molecules (CAM, such as RGD (amino acid sequence Arg-Glu-Asp), laminin, collagen, etc.) in tissue engineering applications or adhesion prevention coatings to be used on medical devices such as vena cava filters or small diameter vascular grafts. Coating material also include infection resistance coatings or antimicrobial containing coating. Some coatings also provide for sustained drug release such as sustained release of drug from stents, or as a hydrophobic overcoat to extend the release time of a drug loaded depot. Bio-active coatings containing therapeutic agents such as heparin, phosphoryl choline (PC), urokinase, etc., are used for antithrombogenic properties.

The coatings can be used to deliver therapeutic and pharmaceutic agents such as, but not limited to: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e.estrogen); Anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); Angiogenic: vascular endothelial growth factor (VEGF), fibroblast growth factor (FGF); nitric oxide donors; anti-sense oligo nucleotides and combinations thereof.

Coating may be formulated by mixing one or more therapeutic agents with the polymeric coating mixture. The therapeutic agent may be present as a liquid, a finely divided solid, or any other appropriate physical form. Optionally, the coating mixture may include one or more additives, e.g., nontoxic auxiliary substances such as diluents, carriers, excipients, stabilizers or the like. Other suitable additives may be formulated with the polymer and pharmaceutically active agent or compound. For example, hydrophilic polymer may be added to a biocompatible hydrophobic coating to modify the release profile, or a hydrophobic polymer may be added to a hydrophilic coating to modify the release profile. One example would be adding a hydrophilic polymer selected from the group consisting of polyethylene oxide (PO), PVP, PEG, carboxymethyl cellulose, and hydroxymethyl cellulose to a hydrophobic (co)polymer coating to modify the release profile. Appropriate relative amounts can be determined by monitoring the in vitro and/or in vivo release profiles for the therapeutic agents.

Methods for surface modification typically include a surface activation step followed by the coupling of the desired molecule. Surface activation is usually achieved by an energy assisted gas phase reaction (plasma, pulsed plasma, flow discharge reactive chemistry (FDRC), corona discharge, etc.) and/or activating the substrate with a highly reactive leaving group (N—OH succinimide, imidizole, etc.); Functionalization of the surface with self-assembly molecules (SAM, functional silanes and thiols); Controlled hydrolysis of the esters and amides at the surface (polyethylene terephthalate (PET), polylactic acid (PLA), polyglycolic acid (PGA), etc.). Coupling reactions are typically accomplished by carbodiimide chemistry, reductive amination, malemide-thiol reactions, etc.

Photochemical surface modifications are usually preferred since this method typically does not require a prior surface activation step. Arylketone based chemistry, azide chemistry, acrylate chemistry are key examples.

Sterilization

Most of the coating methods require several processing steps to accomplish the material coating. Substrates modified by each of these methods also require a sterilization method to finalize the product for use by the manufacturer. This introduces the issue of stability of the modified surface under the sterilization process. Conventional sterilization methods such as steam, radiation, and ethylene oxide negatively impact the activity of the coating. Further, radiation (gamma and e-beam), under the conditions evaluated, were shown to induce no grafting of the active heparin component.

Sterilization methods, such as gamma, e-beam and ethylene oxide have been used to sterilize devices which have been previously coated or surface modified. However, there is a need to do both the grafting coating and sterilization in one process by a mechanism that does not severely impact the activity of the bio-active coating.

SUMMARY OF THE INVENTION

The present invention relates to a method of sterilizing a material including the steps of:
1. applying the material with a bioactive coating containing polymerizable chemical;
2. polymerizing the bioactive coating on the material; and
3. sterilizing the material and the bioactive coating with a sterilization process such as hydrogen peroxide employing gas plasma.

In one embodiment of the invention at least a portion of the polymerizing step and the sterilizing step occur simultaneously. In another embodiment of the invention the method includes grafting the bioactive coating on said material. In a preferred embodiment, at least a portion of the polymerizing step, grafting step, and the sterilizing step occur simultaneously.

In one embodiment of the invention the material may include metal, non-metal, polymer or plastic, elastomer, or biologically derived material. In one embodiment, the material is selected from the group including stainless steel, aluminum, nitinol, cobalt chrome, and titanium. In an alternate embodiment, the material is selected from the group including glass, silica, and ceramic.

In another embodiment of the invention the material is selected from the group including polyacetal, polyurethane, polyester, polytetrafluoroethylene, polyethylene, polymethylmethacrylate, polyhydroxyethyl methacrylate, polyvinyl alcohol, polypropylene, polymethylpentene, polyetherketone, polyphenylene oxide, polyvinyl chloride, polycarbonate, polysulfone, acrylonitrile-butadiene-styrene, polyetherimide, polyvinylidene fluoride, and copolymers and combinations thereof.

In another embodiment of the invention the material is selected from the group including polysiloxane, fluorinated polysiloxane, ethylene-propylene rubber, fluoroelastomer and combinations thereof.

In another preferred embodiment, the material is selected from the group including polylactic acid, polyglycolic acid, polycaprolactone, polyparadioxanone, polytrimethylene carbonate and their copolymers, collagen, elastin, chitin, coral, hyaluronic acid, bone and combinations thereof.

In one embodiment of the invention the bioactive coating is selected from the group including biocompatible coating, infection resistance coating, antimicrobial coating, drug release coating, antithrombogenic coating and lubricious coating.

In one preferred embodiment of the invention, the bioactive coating contains heparin, phophoryl choline, urokinase or rapamycin.

The bioactive coating may include a hydrophilic or hydrophobic coating. In a preferred embodiment, the bioactive coating is selected from the group including polyvinyl pyrrolidone, polyethylene glycol, polypropylene glycol, polyethylene glycol-co-propylene glycol, polyethylene glycol acrylate, polyethylene glycol diacrylate, polyethylene glycol methacrylate, polyethylene glycol dimethacrylate, polyethylene oxide, polyvinyl alcohol, polyvinyl alcohol-co-vinylacetate, polyhydroxyethyl methacrylate, and polyhyaluronic acid, and hydrophilically substituted derivatives, monomers, unsaturated pre-polymers, and uncrosslinked polymers with double bonds thereof.

In another preferred embodiment, the bioactive coating is selected from the group including polytetrafluoroethylene, polyethylene, polypropylene, poly(ethylene terephthalate), polyester, polyamides, polyarylates, polycarbonate, polystyrene, polysulfone, polyethers, polyacrylates, polymethacrylates, poly(2-hydroxyethyl methacrylate), polyurethanes, poly(siloxane)s, silicones, poly(vinyl chloride), fluorinated elastomers, synthetic rubbers, poly(phenylene oxide), polyetherketones, acrylonitrile-butadiene-styrene rubbers, poyetherimides, and hydrophobically substituted derivatives thereof and their precursor monomers.

In a preferred embodiment, the disclosed method of sterilizing and polymerizing a bioactive coating on a material includes the steps of:
1. applying the material with a bioactive coating containing non-polymerized but polymerizable chemical; and
2. simultaneously polymerizing the bioactive coating and sterilizing the material and bioactive coating with a sterilization process which includes hydrogen peroxide employing gas plasma.

In a preferred embodiment, the method further includes the step of grafting the bioactive coating on the material. In a more preferred embodiment, at least a portion of the polymerizing step, grafting step, and the sterilizing step occur simultaneously.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

Figure 1:
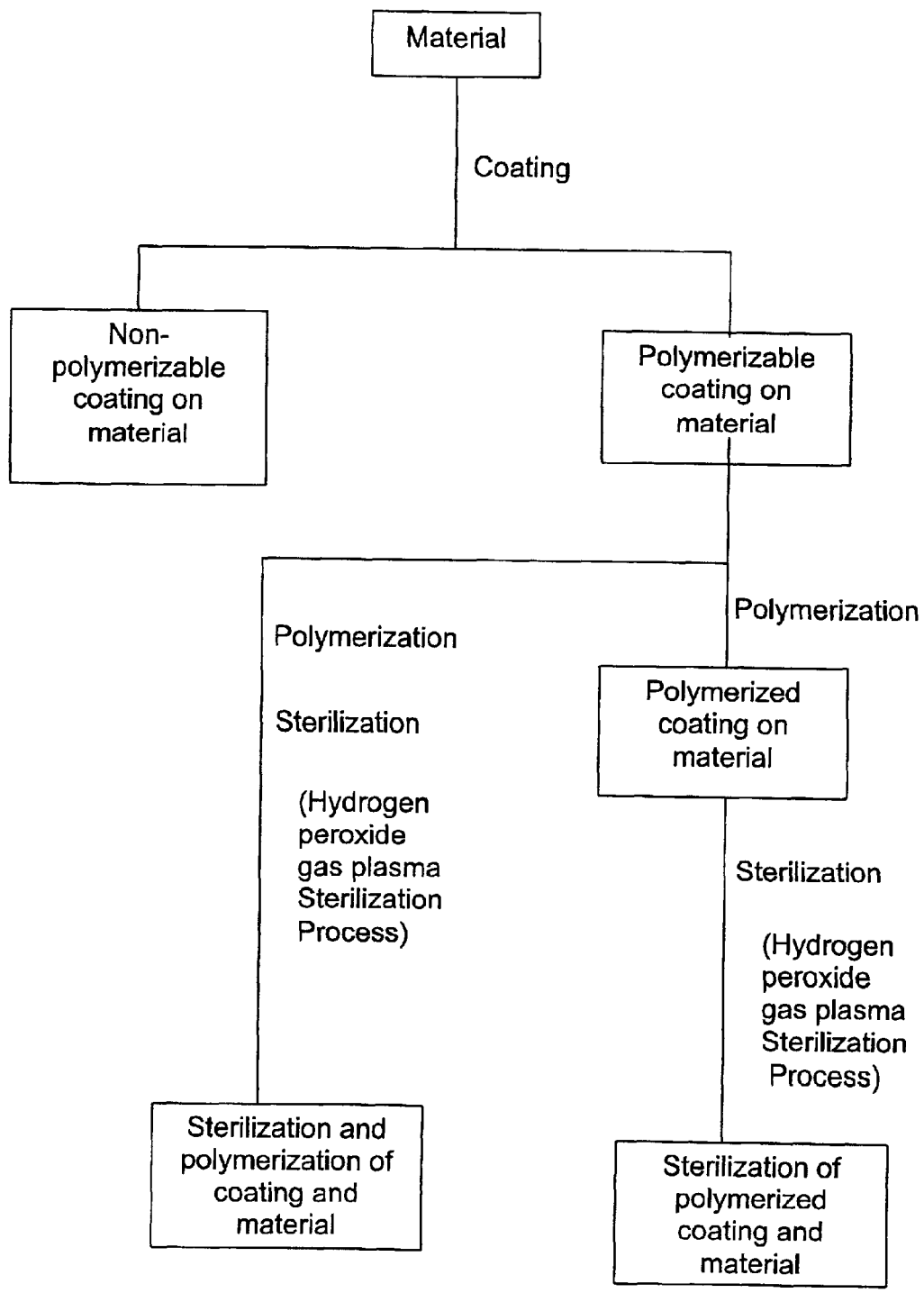
FIG. 1 shows possible approaches to sterilize and polymerize coating and material with a hydrogen peroxide gas plasma sterilization process.

Scenario one: A material is coated, polymerized and grafted with a polymerizable chemical and then sterilized with the hydrogen peroxide gas plasma sterilization process (right side of flow chart).

Scenario two: A material is first coated with a non-polymerized but polymerizable coating and then polymerized and grafted onto the material during the hydrogen peroxide gas plasma sterilization process (middle of flow chart).

Scenario three: If the coating is non-polymerizable, it will not be bound by processing and will be removed or partially removed by aqueous media (washing, implantation, etc.) (left side of flow chart).

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

Coatings applied to materials may be polymerized and covalently bound to the material surface in manufacturing. The coating may be hydrophilic or hydrophobic in nature. This polymerized and grafted coating is resistant to aqueous removal (soaking and rinsing, implantation in aqueous environment) and can be sterilized prior to use. However, many applied coatings that are not covalently bound (van der Waals, electrostatic, surface tension) to material surfaces in processing/manufacture are not resistant to aqueous removal. A polymerizable coating may be covalently bound to the substrate surface by further processing, while a non-polymerizable coating will not be polymerized or grafted to the surface. A further processing step, found to induce polymerization/grafting of a coating to a material surface and sterilize in one step, is sterilization processing with low temperature hydrogen peroxide gas plasma. (FIG. 1). Materials already polymerized and grafted with a coating should also be a good candidate for a further sterilizing process with a hydrogen peroxide gas plasma sterilization system.

This invention provides a method for single-step surface modification. Grafting and sterilization for bio-active coatings on materials and biomaterials used in medical devices, such as catheters, tissue engineering scaffolds, or drug delivery carrier materials is accomplished in a single step. Sterilization of materials that have already been coated, polymerized and grafted is also encompassed by the present invention. These materials may include any medical device or implantable that could benefit from improved antithrombogenic and biocompatible surfaces. Other relevant device examples may include heparin or urokinase coated stents to reduce clotting and restenosis, dental or ophthamological implants. These materials may be comprised of a variety of polymeric or plastic compositions including but not limited to polyacetal, polyurethane, polyester, polyethylene terephthalate, polytetrafluoroethylene, polyvinylidene fluoride, polyarylates, polyethers, polyacrylates, polyethylene, polymethylmethacrylate, polyhydroxyethyl methacrylate (polyHEMA), polyvinyl alcohol, polypropylene, polymethylpentene, polyetherketone, polyphenylene oxide, polyvinyl chloride, polycarbonate, polysulfone, acrylonitrile-butadiene-styrene, polyetherimide, silicones, polysiloxanes, polyvinyl pyrrolidone, polyethylene glycol, polypropylene glycol, polyethylene glycol-co-propylene glycol, polyethylene glycol acrylate, polyethylene glycol diacrylate, polyethylene glycol methacrylate, polyethylene glycol dimethacrylate, polyvinyl alcohol-co-vinylacetate, PLA or PGA, polycaprolactone, polytrimethylene carbonate, polyparadioxinone, and combinations thereof, etc.

The materials may also be metal or non-metal or elastomer. The metal material may be comprised of a variety of metals, including but not limited to, stainless steel, aluminum, nitinol, cobalt chrome, or titanium. The materials may also be elastomeric, including but not limited to polysiloxanes, fluorinated polysiloxane, ethylene-propylene rubber or fluoroelastomers. The substrates can also be inorganics, including but not limited to glass, silica, and ceramics. The material could also be biologically derived, including but not limited to, collagen, elastin, hyaluronic acid, bone, coral or chitan.

Using the STERRAD® (The STERRAD Sterilization system manufactured and trademarked by Advanced Sterilization Products, a Johnson & Johnson company) low temperature hydrogen peroxide gas plasma sterilization process (see, for example, U.S. Pat. No. 5,656,238 which is herein incorporated by reference), the surface modification, grafting and sterilization, can be accomplished in one step without inactivating the bio-active coating. Other sterilization methods such as steam, radiation, and ethylene oxide negatively impact the activity of the coating. Further, radiation (gamma and e-beam) were shown to induce no incorporation of the active heparin component. The STERRAD sterilization process induces the grafting (necessary for adhesion/chemical bonding) of the coating to the surface of the material. The second benefit is that sterilization is accomplished in the same process without degradation of the bio-activity.

A novel technique of surface modification and sterilization in a single step has been identified. This method can be applied to a wide range of biomaterials, including catheters coated with bio-active coating. In the specific experimentation, polyurethane catheters cleaned BIO-VUE™ catheters (The BIOVUE catheter manufactured and trademarked by Johnson & Johnson Medical, Inc.) were dip-coated in a dilute aqueous Tween solution (0.5% w/w) of PEG acrylate (ACRL 34,000 MW, Shearwater Polymers), hyaluronic acid (Lifecore Tenalure, un-crosslinked sodium hyaluronate, catalog # 1011-1106) and heparin sodium salt. Sterilization was accomplished by the STERRAD Sterilization system. Chemical grafting (incorporation of heparin to the catheter) or entrapment was demonstrated by x-ray photon spectroscopy (XPS) and in-vitro anticoagulant property was demonstrated (coating functionality) by an inactivated partial thromboplastin test (UPTT). The combined sterilization/grafting may also demonstrate a synergistic effect in that the pre-coated substrates were also subjected to argon plasma (only) systems, which showed some but minimal grafting. Moreover, the effectiveness of an argon plasma for sterilization has not been demonstrated.

The process provides a means to do the following:
Sterilization of catheters and other bio-active coated medical devices
One-step process for sterilization of devices and grafting of the active coating component
The process induces grafting of the heparin coating to the medical device surface, unlike other sterilization methods
The process does not cause degradation of the bio-active coating, as do other sterilization methods
The current invention obviates the need for multiple processing steps. A specific, commercially available sterilization method has been used to introduce chemical grafting to biomaterials. Therefore, the stability issue under sterilization is avoided. The surface chemical grafting or entrapment was demonstrated by XPS analysis following an accelerated phosphate buffered saline (PBS) aging protocol (challenge). The functionality of the heparin-PEG surface was also demonstrated by the UPTT assay. Further, sterilization efficiency was demonstrated using a biological indicator. Details of these experiments are in the examples below.

EXAMPLES

The invention is further illustrated by the following non-limiting examples.

Example 1

XPS data was collected to indicate coating coverage of the substrate. A higher Oxygen/Carbon (O/C) value would indicate significant PEG on the surface. This is indicative of a higher amount of coating on the surface. The sulfur (S) value is indicative of the heparin, the active component of the coating, on the surface. Challenged samples were exposed to a PBS soak at 45° C. for two hours to remove any unbound heparin, then rinsed with deionized water (DI), prior to XPS analysis.

TABLE 1

Controls for Study - The control samples demonstrate the baseline values for later comparison to treatments. This demonstrates that a significant fraction of the heparin can be liberated by challenging because it is not bound to the surface.

| Exposure Technique | % Atoms on Surface Detected by XPS | |
|---|---|---|
| | O/C* | S^ |
| Cleaned Biovue ™ control (uncoated catheter control) | 0.26 | 0.04 |
| Coated/not challenged | 0.32 | 0.32 |
| Coated/challenged | 0.26 | 0.14 |

XPS data are generally reported to one significant digit beyond the decimal point. For the early data, results were reported to one significant digit. The later data were reported to two significant digits so that 0.24 and 0.26 are not thought to differ by a factor of 1.5, i.e. 0.2 vs. 0.3.
*O/C numbers higher than the control are indicative of a PEG group on the surface (PEG having more oxygen than PU); detection of coating on surface.
^S is indicative of heparin on the surface.

Example 2

The following Table 2 shows that for the STERRAD Sterilization process, PEG incorporation (O/C) and heparin grafting (S) were higher compared to other processes. The coating solution was a 1:1 dilution of PEG Acrylate (1.9%w/w) +heparin (2.85%w/w) +hyaluronic acid (0.5%w/w) in solution of 0.5% Tween® (Tween manufactured and trademarked by ICI Americas, Inc.) in DI $H_2O$. Challenged samples were exposed to a phosphate buffered saline (PBS) soak at 45° C. for two hours to remove any unbound heparin and rinsed with DI water prior to XPS analysis. The STERRAD sterilization cycle parameters were 15 minutes air plasma, 500W; 6 minutes injection time (1.8 ml, 59% hydrogen peroxide); 5 minutes diffusion at atmospheric pressure; 2 minute hydrogen peroxide plasma. The STERRAD 200 Sterilizer was used for all testing.

TABLE 2

Comparison to other sterilization methods

| Exposure Technique | % Atoms on Surface Detected by XPS after PBS challenge | |
|---|---|---|
| | O/C* | S^ |
| Gamma sterilization (5 Mrad) | 0.1 | 0.04 |
| e-beam sterilization (5 Mrad) | 0.13 | 0.04 |
| STERRAD Sterilization grafted (500W) | 0.40 | 0.26 |

XPS data are generally reported to one significant digit beyond the decimal point. For the early data, results were reported to one significant digit. The later data were reported to two significant digits so that 0.24 and 0.26 are not thought to differ by a factor of 1.5, i.e. 0.2 vs. 0.3.
*O/C numbers higher than the control are indicative of a PEG group on the surface (PEG having more oxygen than PU); detection of coating on surface.
^S is indicative of heparin on the surface.

Example 3

Table 3 shows that for the STERRAD Sterilization process, higher PEG incorporation (O/C) and heparin grafting (S) resulted over the Argon plasma process alone. Moreover, the effectiveness of an argon plasma for sterilization has not been demonstrated. The coating solution was a 1:1 dilution of PEG Acrylate (1.9%w/w) +heparin (2.85%w/w) in solution of 0.5% Tween in DI $H_2O$. Challenged samples were exposed to a PBS soak at 45° C. for two hours to remove any unbound heparin and rinsed with DI water prior to XPS analysis.

TABLE 3

Comparison to plasma only technique

| Exposure Technique | % Atoms on Surface Detected by XPS after PBS challenge | |
|---|---|---|
| | O/C* | S^ |
| Argon plasma (75W, 300 mtorr, 5 min.) | 0.32 | 0.1 |
| STERRAD Sterilization grafted (500W) | 0.40 | 0.26 |

XPS data are generally reported to one significant digit beyond the decimal point. For the early data, results were reported to one significant digit. The later data were reported to two significant digits so that 0.24 and 0.26 are not thought to differ by a factor of 1.5, i.e. 0.2 vs. 0.3.
*O/C numbers higher than the control are indicative of a PEG group on the surface (PEG having more oxygen than PU); detection of coating on surface.
^S is indicative of heparin on the surface.

Example 4

The STERRAD Sterilization process induced PEG incorporation (O/C) and heparin grafting (S) reproducibly. Challenged controls indicated that the heparin was not grafted. The STERRAD Sterilization processed samples indicated higher PEG incorporation (O/C) and heparin grafting (S). Reproducibility was demonstrated.

The coating solution was a 1:1 dilution of PEG Acrylate (1.9%w/w) +heparin (2.85%w/w) +hyaluronic acid (0.5%w/w) in solution of 0.5% Tween in DI $H_2O$. Challenged samples were exposed to a PBS soak at 45° C. for two hours to remove any unbound heparin and rinsed with DI water prior to XPS analysis.

TABLE 4

Comparison to controls

| Exposure Technique | % Atoms on Surface Detected by XPS | |
|---|---|---|
| | O/C* | S^ |
| Cleaned Biovue ™ control uncoated/exposed to STERRAD | N.A.** | 0.06 |
| Coated/not exposed to STERRAD/challenged | 0.26 | 0.14 |
| STERRAD Sterilization (500W) grafted-PBS challenge | N.A.** | 0.28 |
| STERRAD Sterilization (500W) grafted-PBS challenge | 0.40 | 0.26 |
| STERRAD Sterilization (500W) grafted-PBS challenge (retain from example 2) | N.A.** | 0.25 |
| STERRAD Sterilization (500W) grafted-PBS challenge (retain from example 2) | N.A.** | 0.29 |

XPS data are generally reported to one significant digit beyond the decimal point. For the early data, results were reported to one significant digit. The later data were reported to two significant digits so that 0.24 and 0.26 are not thought to differ by a factor of 1.5, i.e. 0.2 vs. 0.3.
*O/C numbers higher than the control are indicative of a PEG group on the surface (PEG having more oxygen than PU); detection of coating on surface.
^ S is indicative of heparin on the surface.
**N.A. = not available

Example 5

To demonstrate the efficacy of sterilization, the same coated catheter sample surfaces were exposed to the STERRAD sterilization process. The coating solution was a 1:1 dilution of PEG Acrylate (1.9%w/w) +heparin (2.85%w/w) +hyaluronic acid (0.5%w/w) in solution of 0.5% Tween in DI H$_2$O. Half cycle parameters were 15 minutes air plasma, 500W; 3 minutes injection time (1.8 ml, 59% hydrogen peroxide); 2.5 minutes diffusion at atmospheric pressure; and 1 minute hydrogen peroxide plasma. The STERRAD 200 Sterilizer was used for all testing. The process was challenged with biological indicators. Biological indicators (glass fiber disk challenged with $10^6$ B. stearothermophilus) were placed with the device sample in a sealed Tyvek® /film pouch (Tyvek is manufactured and trademarked by E. I. du Pont de Nemours and Company). The following results indicate efficacious sterilization.

TABLE 5

Sterilization efficacy of biologically challenged samples.

| sample | RESULTS OF BIOLOGICAL INDICATORS |
|---|---|
| 1 | negative for biological growth |
| 2 | negative for biological growth |
| 3 | negative for biological growth |
| 4 | negative for biological growth |
| Unprocessed control | positive for biological growth |

Example 6

The UPPT in-vitro efficacy test was done as evidence of retention of function of the heparin (heparin activity) after exposure to the process. The coating solution was a 1:1 dilution of PEG Acrylate (1.9%w/w) +heparin (2.85%w/w) +hyaluronic acid (0.5%w/w) in solution of 0.5% Tween in DI H$_2$O.

TABLE 6

UPTT assay
In vitro anticoagulant property is demonstrated by the UPTT. The UPTT measures the blood clotting time, demonstrating greater incorporated anticoagulant effect on the STERRAD sterilization processed sample than the control.

| Exposure Technique | UPTT in-vitro efficacy test (% of untreated blood plasma control) (Time in seconds) |
|---|---|
| STERRAD Sterilization Process (500W) | >330 (>148%) |
| Cleaned Biovue ™ control (uncoated catheter control) | 204+/−16 (92%) |

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of sterilizing a medical device comprising:
   applying a bioactive coating comprising polymerizable chemical to said medical device;
   polymerizing said bioactive coating on said medical device; and simultaneously or thereafter
   sterilizing said medical device and said bioactive coating with a sterilization process comprising generating a hydrogen peroxide gas plasma, without significantly impacting the bio-activity of the coating.

2. The method of claim 1, wherein at least a portion of the polymerizing step and the sterilizing step occur simultaneously.

3. The method of claim 1 further comprising grafting said bioactive coating on said medical device.

4. The method of claim 3, wherein at least a portion of the polymerizing step, grafting step, and the sterilizing step occur simultaneously.

5. The method of claim 1, wherein the medical device comprises metal, non-metal, polymer or plastic, elastomer, or biologically derived material.

6. The method of claim 1, wherein the medical device comprises a material selected from the group consisting of stainless steel, aluminum, nitinol, cobalt chrome, and titanium.

7. The method of claim 1, wherein the medical device comprises a material selected from the group consisting of glass, silica, and ceramic.

8. The method of claim 1, wherein the medical device comprises a material selected from the group consisting of polyacetal, polyurethane, polyester, polytetrafluoroethylene, polyethylene, polymethylmethacrylate, polyhydroxyethyl methacrylate, polyvinyl alcohol, polypropylene, polymethylpentene, polyetherketone, polyphenylene oxide, polyvinyl chloride, polycarbonate, polysulfone, acrylonitrile-butadiene-styrene, polyetherimide, polyvinylidene fluoride, and copolymers and combinations thereof.

9. The method of claim 1, wherein the medical device comprises a material selected from the group consisting of polysiloxane, fluorinated polysiloxane, ethylene-propylene rubber, fluoroelastomer and combinations thereof.

10. The method of claim 1, wherein the medical device comprises a material selected from the group consisting of polylactic acid, polyglycolic acid, polycaprolactone, polyparadioxanone, polytrimethylene carbonate and their copolymers, collagen, elastin, chitin, coral, hyaluronic acid, bone and combinations thereof.

11. The method of claim 1, wherein the bioactive coating is selected from the group consisting of biocompatible coating, infection resistance coating, antimicrobial coating, drug release coating, antithrombogenic coating and lubricious coating.

12. The method of claim 1, wherein the bioactive coating comprises heparin, phophoryl choline, urokinase or rapamycin.

13. The method of claim 1, wherein the bioactive coating comprises a hydrophilic or hydrophobic coating.

14. The method of claim 1, wherein the bioactive coating comprises a polymer selected from the group consisting of polyvinyl pyrrolidone, polyethylene glycol, polypropylene glycol, polyethylene glycol-co-propylene glycol, polyethylene glycol acrylate, polyethylene glycol diacrylate, polyethylene glycol methacrylate, polyethylene glycol dimethacrylate, polyethylene oxide, polyvinyl alcohol, polyvinyl alcohol-co-vinylacetate, polyhydroxyethyl methacrylate, and polyhyaluronic acid, and hydrophilically substituted derivatives, monomers, unsaturated prepolymers, and uncrosslinked polymers with double bonds thereof.

15. The method of claim 1, wherein the bioactive coating comprises a polymer selected from the group consisting of polytetrafluoroethylene, polyethylene, polypropylene, poly(ethylene terephthalate), polyester, polyamides, polyarylates, polycarbonate, polystyrene, polysulfone, polyethers, polyacrylates, polymethacrylates, poly(2-hydroxyethyl methacrylate), polyurethanes, poly(siloxane)s, silicones, poly(vinyl chloride), fluorinated elastomers, synthetic rubbers, poly(phenylene oxide), polyetherketones, acrylonitrile-butadiene-styrene rubbers, poyetherimides, and hydrophobically substituted derivatives thereof and their precursor monomers.

16. A method of sterilizing and polymerizing a bioactive coating on a medical device comprising:

applying a bioactive coating comprising non-polymerized but polymerizable chemical to said medical device; and simultaneously polymerizing said bioactive coating and sterilizing said medical device and bioactive coating with a sterilization process comprising generating a hydrogen peroxide gas plasma, without significantly impacting the bioactivity of the coating.

17. The method of claim 16 further comprising grafting said bioactive coating on said medical device.

18. The method of claim 17, wherein at least a portion of the polymerizing step, grafting step, and the sterilizing step occur simultaneously.

19. A method of sterilizing a material comprising:

applying a bioactive coating comprising polymerizable chemical to said material;

polymerizing said bioactive coating on said material; and simultaneously or thereafter sterilizing said material and said bioactive coating with a sterilization process comprising generating a hydrogen peroxide gas plasma with a frequency of 0.1 MHz to 30 MHz, without significantly impacting the bio-activity of the coating.

20. A method of sterilizing a material comprising:

applying a bioactive coating comprising polymerizable chemical to said material;

polymerizing said bioactive coating on said material; and simultaneously or thereafter sterilizing said material and said bioactive coating with a sterilization process comprising generating a hydrogen peroxide gas plasma, without significantly impacting the bio-activity of the coating, wherein the material is selected from the group consisting of stainless steel, aluminum, nitinol, cobalt chrome, and titanium.

21. A method of sterilizing a material comprising:

applying a bioactive coating comprising polymerizable chemical to said material;

polymerizing said bioactive coating on said material; and simultaneously or thereafter sterilizing said material and said bioactive coating with a sterilization process comprising generating a hydrogen peroxide gas plasma, without significantly impacting the bio-activity of the coating, wherein the material is selected from the group consisting of polylactic acid, polyglycolic acid, polycaprolactone, polyparadioxanone, polytrimethylene carbonate and their copolymers, collagen, elastin, chitin, coral, hyaluronic acid, bone and combinations thereof.

22. A method of sterilizing a material comprising:

applying a bioactive coating comprising polymerizable chemical to said material;

polymerizing said bioactive coating on said material; and simultaneously or thereafter sterilizing said material and said bioactive coating with a sterilization process comprising generating a hydrogen peroxide gas plasma, without significantly impacting the bio-activity of the coating, wherein the bioactive coating comprises heparin, phophoryl choline, urokinase or rapamycin.

23. A method of sterilizing a material comprising:

applying a bioactive coating comprising polymerizable chemical to said material;

introducing a biological indicator;

polymerizing the bioactive coating on the material; and sterilizing the material with the bioactive coating and the biological indicator with a sterilization process comprising generating a hydrogen peroxide gas plasma.

* * * * *